(12) United States Patent
Lauber (10) Patent No.: US 7,831,083 B1
(45) Date of Patent: Nov. 9, 2010

(54) IMAGE QUALITY MONITORING FOR SUBSTRATE INSPECTION

(75) Inventor: Jan Lauber, San Francisco, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 963 days.

(21) Appl. No.: 11/457,213

(22) Filed: Jul. 13, 2006

(51) Int. Cl.
*G06K 9/00* (2006.01)
*G06K 9/48* (2006.01)
(52) U.S. Cl. ....................... 382/141; 382/199
(58) Field of Classification Search .......... 382/141–152
See application file for complete search history.

(56) References Cited

U.S. PATENT DOCUMENTS

| | | | | |
|---|---|---|---|---|
| 4,578,713 A | * | 3/1986 | Tsao et al. | 358/3.07 |
| 5,963,654 A | * | 10/1999 | Prakash et al. | 382/112 |
| 6,252,981 B1 | * | 6/2001 | Guest et al. | 382/149 |
| 6,990,219 B2 | * | 1/2006 | Morimura et al. | 382/125 |
| 2002/0009220 A1 | * | 1/2002 | Tanaka | 382/145 |
| 2004/0008903 A1 | * | 1/2004 | Kim | 382/274 |
| 2005/0213842 A1 | * | 9/2005 | Aldrich et al. | 382/264 |

* cited by examiner

*Primary Examiner*—Vu Le
*Assistant Examiner*—Alex Liew
(74) *Attorney, Agent, or Firm*—Joshua D. Isenberg; JDI Patent (57) ABSTRACT

A method for monitoring the stability of an inspection or processing of a substrate, a substrate inspection system and a processor readable medium are disclosed. One or more images of one or more portions of the substrate may be obtained from an inspection tool. Image quality information may be extracted from the one or more images. The image quality information may be analyzed to monitor stability of the inspection tool and/or to determine variation of a process performed on the substrate.

30 Claims, 5 Drawing Sheets

IMAGE QUALITY MONITORING FOR SUBSTRATE INSPECTION

FIELD OF THE INVENTION

This invention is related to substrate inspection and more particularly to monitoring the stability of an inspection apparatus or substrate process.

BACKGROUND OF THE INVENTION

Fabricating semiconductor devices such as logic and memory devices typically includes processing a substrate such as a semiconductor wafer using a number of semiconductor fabrication processes to form various features and multiple levels of the semiconductor devices. Processed substrates, e.g., semiconductor wafers, are often inspected after processing to determine whether there are any defects. An inspection tool may scan a substrate and collect images of selected portions of the substrate that are suspected to contain defects. Such images are sometimes referred to as patch images. After an inspection scan has completed a user can review the patch images to determine whether defects are present.

It is within this context that embodiments of the present invention arise.

BRIEF DESCRIPTION OF THE DRAWINGS

Other objects and advantages of the invention will become apparent upon reading the following detailed description and upon reference to the accompanying drawings in which.

DESCRIPTION OF THE SPECIFIC EMBODIMENTS

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention.

According to embodiments of the present invention image quality information may be quantified and analyzed to measure inspection tool or process stability. Patterns observed in the image quality information may be correlated to stability of an inspection of a substrate or process variations across a substrate. Process variations may occur across a substrate within a scan. Tool variations may occur within a single scan or from scan to scan over time. Embodiments of the invention allow for image quality monitoring in a substrate inspection tool. Image quality may be monitored of a range of time scales. For example, image quality may be monitored within a single scan taken, e.g., over a period of one or more hours. Alternatively, image quality may be monitored over several weeks or months of tool operation or over a period between tool calibrations (e.g., about one month).

Figure 1:
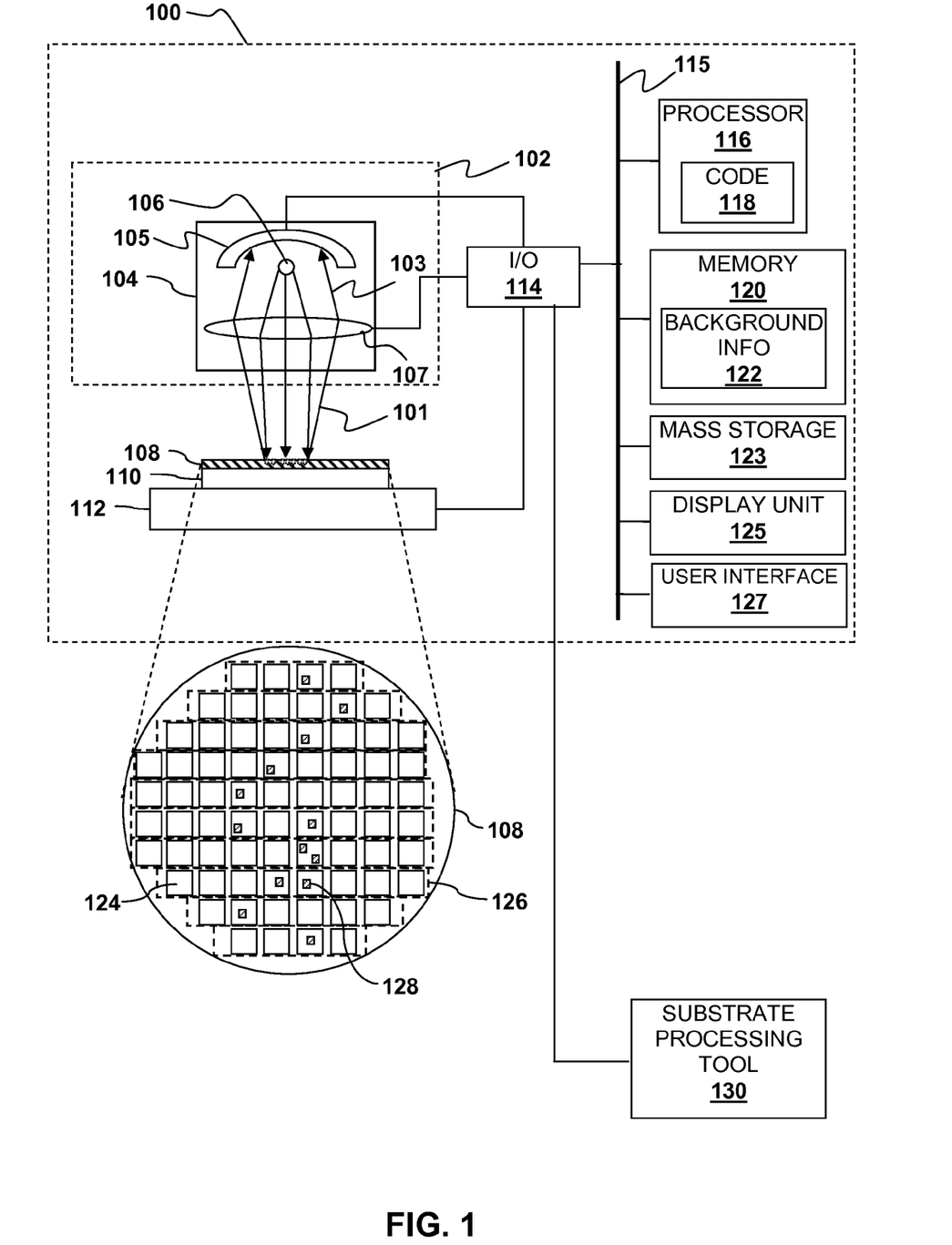
FIG. 1 is a block diagram of a substrate inspection system according to an embodiment of the present invention.
Figure 2:
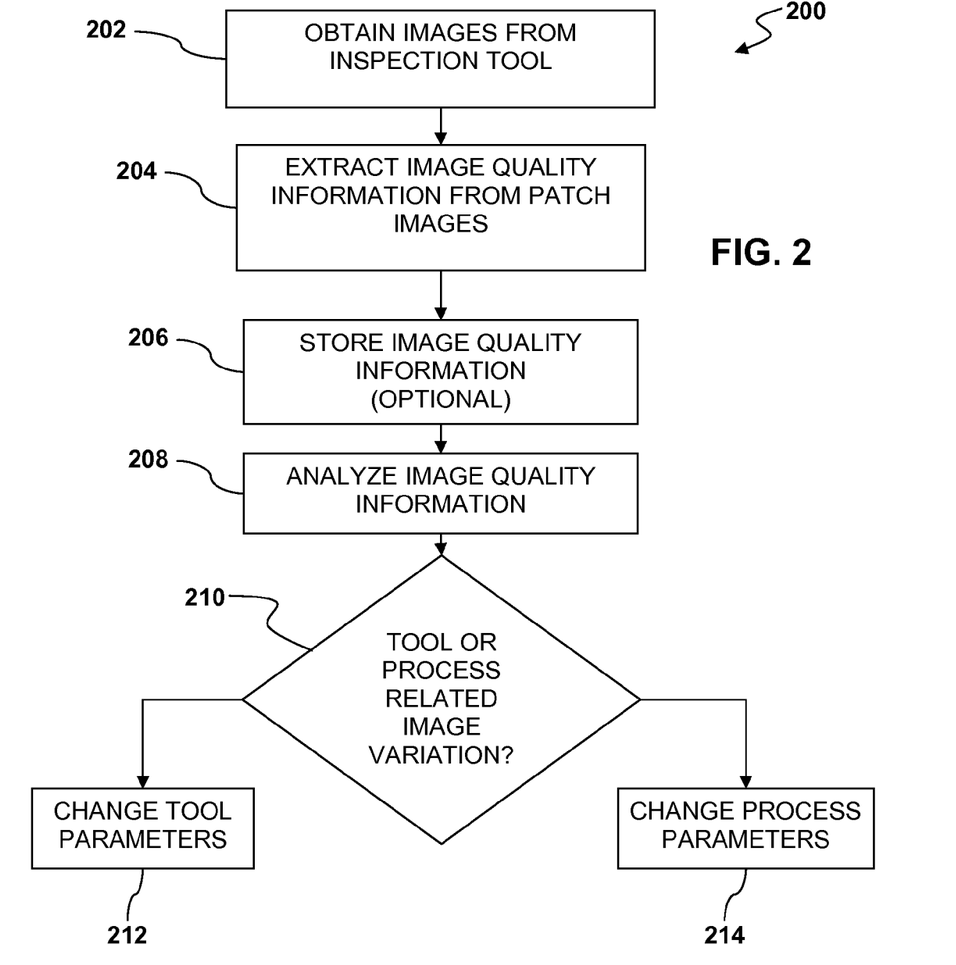
FIG. 2 is a flow diagram illustrating a method for monitoring the stability of an inspection of a substrate according to an embodiment of the present invention.

Embodiments of the invention may be understood by referring simultaneously to FIG. 1 and FIG. 2. FIG. 1 depicts a block diagram of a substrate inspection system 100 and FIG. 2 depicts a flow diagram of a method 200 for monitoring the stability of an inspection of a substrate. The system 100 generally includes a wafer inspection tool 102 having an image capture unit 104. The inspection tool 102 may be any suitable inspection tool used for inspecting substrates. Examples of such tools include optical microscopes and electron microscopes, scanning probe microscopes including scanning tunneling microscopes, atomic force microscopes and the like. Other examples include surface inspection tools that utilize electric or magnetic probes or scanning substrates with lasers and detecting laser light scattered from the substrate.

By way of example, the image capture unit 104 may include a radiation source 106 and optics 107 that focus radiation 101 (e.g., photons or electrons) from the source 106 onto a surface of a substrate 108. The optics 107 may focus return radiation 103 from the substrate 108 onto a sensor 105 to obtain images of the surface of the substrate 108. By way of example the image capture unit 104 may include sensor or array of sensors, such as a charge-coupled device, that produces electronic (e.g., digital) signals in proportion to the intensity of the return radiation. The inspection tool 102 may include a substrate support 110 that retains the substrate 108 during image capture. By way of example, the substrate support 110 may include a chuck, e.g., an electrostatic chuck, magnetic chuck or vacuum chuck, depending on the type of tool. The support 110 may include or be mounted to a translation mechanism 112, e.g., a stepper. The translation mechanism 112 may translate the substrate 108 with respect to the image capture unit 104. Such translation may take place in a plane parallel to the substrate and or perpendicular to the substrate and may include rotation of the substrate about an axis. Alternatively, the inspection tool may include a mechanism that translates the image capture unit 104 relative to the substrate 108.

Input output (I/O) elements 114 and a data bus 115 may couple the image capture unit 104 and other components of the inspection tool 102 to a processor 116. The processor 116 may operate in response to coded instructions 118, which may cause the system 100 to monitor the stability of an inspection or processing of the substrate 108, e.g., in accordance with the method 200 or relevant portions thereof. The coded instructions 118 may conform to any one of a number of different programming languages such as Assembly, C++, JAVA or any of a number of other programming languages. The processor 116 may be a general purpose computer that becomes a special purpose computer when running the code instructions 118. The coded instructions 118 may be embodied in any suitable processor readable medium, e.g., a memory 120 or mass storage device 123, which may be coupled to the processor 116, e.g., via the data bus 115. By way of example, the memory 120 may be any suitable form of electronic memory, e.g., RAM, DRAM, ROM, flash memory and the like. The mass storage device 123 may be any suitable type of data storage device such as a magnetic disk drive, optical disk drive, CD-ROM drive, tape drive, flash memory and the like to store programs and/or data. The coded instructions 118 may be retrieved by the processor 116 for execution. Data generated and/or used by the coded instructions 118 may be stored in a memory unit 120 or mass storage device 123.

The system 100 may optionally include a display unit 125 and user interface unit 127 to facilitate interaction between the system 100 and a user. The display unit 125 may be in the form of a cathode ray tube (CRT), flat panel screen, printer or other device that displays text, numerals, or graphical symbols. The user interface 127 may include a keyboard, mouse, joystick, light pen or other device. These components may be operably coupled with each other and with the processor 116 and/or memory 120 the system bus 115.

The inspection tool 102 generates images of the substrate, or portions thereof, to facilitate inspection. For example, the substrate 108 may be made up of multiple dies 124. Each die 124 may include a semiconductor integrated circuit at an intermediate stage of manufacture. The inspection tool may obtain images of each die 124. Translation of the substrate 108 relative to the image capture unit (or vice versa) may facilitate generation of images of narrow sections of the substrate. Such images are referred to as swath images 126. Each swath image 126 may encompass several die 124. Each swath image 126 may be made up of a large number of pixels. Each pixel may have associated with it information relating to its location, a brightness value, an optional color value and other information.

A typical swath image 126 may correspond to several hundred gigabytes of digital data. Analysis and storage of such large images may be problematic. Fortunately, defects on the substrate 108 are usually relatively small compared to the size of the swath images 126. Analysis of defects therefore typically requires analysis of an image of a relatively small area in the vicinity of a suspected defect. Such images are referred to as patch images 128. Generally, but not invariably, if there are no defects, no patch images 128 are generated by the inspection tool 102. By way of example, and without limitation, the patch images 128 may be generated from the swath images 126 by performing an inspection on a whole swath image 126. If any pixel or group of pixels exceeds some limit, they may be flagged and the portion of the swath image 126 around the flagged pixels may be saved in the form of a patch image 128, which may be used for further processing. Patch images 128 generated in this way are sometimes referred to as defective patches images. Alternatively patch images 126 may be collected at pre-defined locations on each die for the purpose of monitoring the inspection or process quality. Patch images 128 generated in this way are sometimes referred to as forced patch images. In addition the patch images 128 may include one or more reference patch images. As used herein a reference patch image refers to a patch image collected together with the defective patch images from some non-defective area, e.g., in a different die or different cell. Analysis of patch images may be performed on either a defective patch image or a reference patch image. In the latter case, the analysis is not influenced by the defect itself.

Typical patch images may range from about 32 by 32 pixels to about 128 by 128 pixels, commonly about 64 by 64 pixels. The patch images 128 represent several orders of magnitude less data than the swath images 126.

In the prior art, histograms of the brightness of the swath images 126 at each die 124 were used to adjust an initial image gain of an inspection tool and then promptly discarded. This is because wafer inspection previously concentrated on analysis of defects and images of defects. Image quality information, such as the brightness histograms, was discarded. Embodiments of the present invention, by contrast, may utilize such image quality information from the images to diagnose potential problems in the inspection tool 102 and or a processing tool 130 that processed the substrate 108 prior to inspection.

According to an embodiment, images may be obtained from the inspection tool 102, as indicated at block 202 of FIG. 2. Image quality information 122 may be extracted from images, such as the swath images 126 or patch images 128, as indicated at block 204. The image quality information 122 may take on any suitable form. The image quality information 122 may be extracted from one or more images (e.g., entire swath images 126, patch images 128 or other images) during the course of an inspection with the inspection tool 102. The image quality information 122 may optionally be stored in the memory 120 for later analysis, as indicated at block 206. The image quality information 122 may be analyzed to monitor a stability of the inspection tool and/or to determine a process variation across the substrate as indicated at block 208. The results of the analysis of the image quality information 122 performed at block 208 may be used to monitor stability of the tool 102 and/or to determine variation of a process performed on the substrate 108.

There are a number of different ways to use the results of the analysis. For example, from the image analysis at block 208 it may be determined whether variations in an image are tool-related or process-related, as indicated at block 210. Analysis of variation of the image quality information may be used to determine whether the variation in the image quality information 122 results from the inspection tool or a process performed on the substrate. For example, variation of the image quality information 122 with respect to time during a scan may indicate a problem with the tool. Similarly, variations in the image quality information 122 with respect to location on the substrate may indicate a variation in the substrate process. Corrective measures may be taken in response to analysis of the image quality information. For example, if the problem is tool related, tool parameters may be adjusted, as indicated at block 212. Alternatively, if the problem is process-related, parameters of a processing tool 130 may be adjusted, as indicated at block 214.

Generally, the image quality information 122 represents information that would ordinarily be discarded when analyzing an image for defects. Examples of such image quality information 122 include, but are not limited to, image quality values such as brightness, contrast, sharpness or capture rate for images of the substrate 108 or portions thereof, e.g., a patch image, die image or swath image). The image quality information 122 may be extracted by generating one or more histograms of image quality values during the course of an inspection with the tool 102. One or more average image quality values may be determined from the histogram(s).

Figure 3:
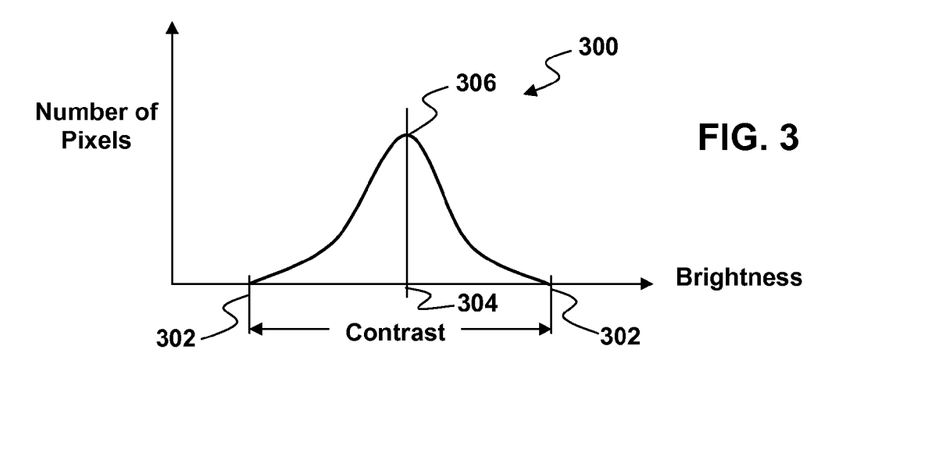
FIG. 3 is a histogram of image brightness illustrating the use of such histograms in monitoring the stability of an inspection or processing of a substrate in accordance with an embodiment of the present invention.

By way of example, and without loss of generality, image quality information may be obtained from histograms of image brightness. As illustrated in FIG. 3, a histogram 300 for an image may plot the number of pixels in the image having a given brightness as a function of brightness. By way of example, the histogram 300 may be one that is conventionally generated during an initial gain adjustment of the inspection tool and saved in the memory 120 instead of being discarded. The histogram 300 may be characterized by a dark histogram endpoint 302 representing a lowest brightness value (or darkest grey level) for the histogram 300. The histogram 300 may be further characterized by a bright histogram endpoint 304 representing a highest brightness value (or brightest grey level) for the histogram 300. The histogram 300 may also be characterized by an average brightness value 306, e.g., a mean, median or mode of the brightness values of all the pixels in the image. In addition the histogram 300 may also be characterized by a brightness range between the dark endpoint 302 and the bright endpoint 304, sometimes referred to as the contrast of the image. The histogram 300 may also be characterized by other statistical measures, such as the spread, variance or standard deviation of the gray level distribution in the images. Any or all of which may be part of the image quality information 122 and any or all of them may be analyzed and the results of the analysis used to monitor tool stability and/or process variation.

There are a number of different ways of analyzing the image quality information 122 and using the results of the analysis. For example the image quality information 122 may be analyzed by determining average quantities for a patch image, die image or swath image. Such average quantities may be graphically displayed in a manner that reveals variations in the average quantities. Such variations may be a variations with respect to time, e.g., from one wafer to another. Alternatively, the variation may be with respect to location on a single wafer.

Figure 4A:
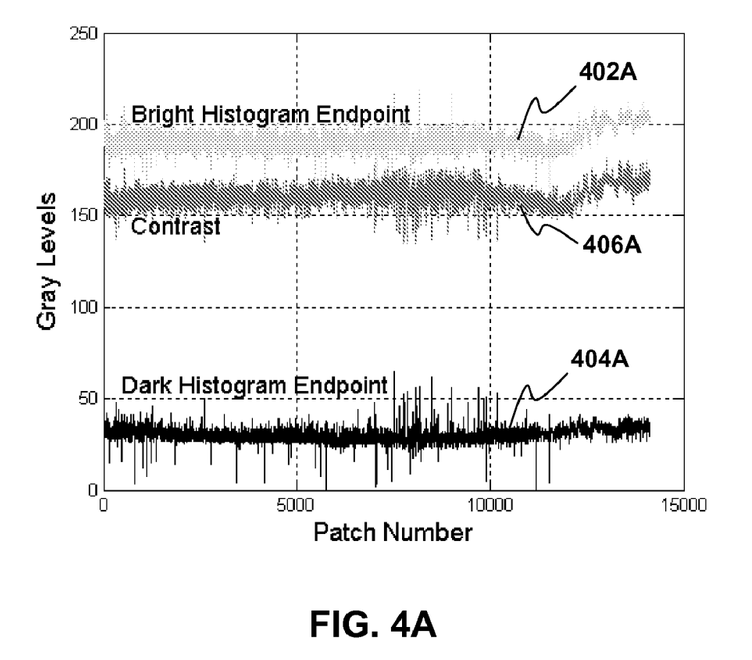
FIGS. 4A-4B are graphs depicting plots of grey level as a function of patch number illustrating an example of monitoring stability of an inspection or processing of a substrate according to an embodiment of the present invention.
Figure 4B:
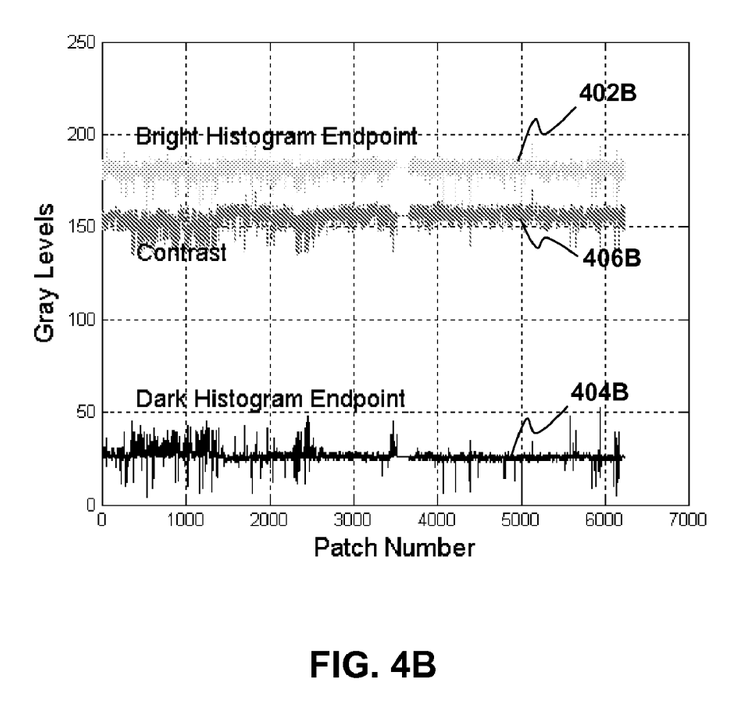

Analysis of the image quality information at block 208 to generate such average quantities and subsequent use of the average quantities may take on any suitable form. For example, grey levels for multiple related images may be calculated and then plotted on a graph for analysis. Such graphs may be presented on the display unit 125 for interpretation by a user. By way of example, the grey levels may represent, e.g., average brightness levels or other brightness values of significance. For example, FIGS. 4A-4B depict plots of bright and dark histogram endpoints and contrast for each patch image taken from a particular wafer. In FIGS. 4A-4B, the endpoint and contrast levels are plotted as a function of patch number. It is noted that the patch number may be related to the time at which the patch image was obtained and may also be related to the location on the substrate 108 of the patch image.

Bright endpoint plots 402A, 402B may correspond to an oxide on a wafer. Dark endpoint plots 404A, 404B may correspond, e.g., to contacts on the wafer. Contrast plots 406A, 406B are also shown in FIG. 4A and FIG. 4B respectively. FIG. 4A illustrates an example of grey level variations across an inspection. Note particularly the rise in the grey level plots 402A, 404A, and contrast plot 406A between about patch number 10000 and patch number 15000. In this case, the changes in brightness and contrast were due to charging of the substrate. Correcting measures involving adjustment of the charge-control parameters of the tool were subsequently implemented. After the correcting measures had been implemented, the gray levels in plots 402B, 404B and 406B became more constant, as seen in FIG. 4B.

Figure 5A:
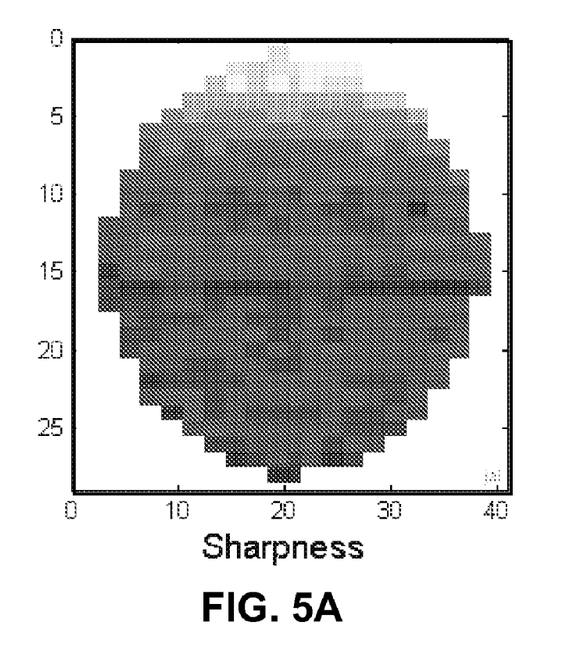
FIG. 5A is map depicting mean sharpness of images of dies on a wafer illustrating another example of monitoring stability of an inspection of a substrate according to an embodiment of the present invention.

There are other ways of analyzing image quality information and presenting results of the analysis to diagnose problems with tool operation or substrate processing. As an example of diagnosing tool performance, FIG. 5A depicts a map of mean sharpness for every die on a wafer. Sharpness is generally defined as a slope in grey scale level. Mean or average sharpness may be defined as a difference in grey scale for neighboring pixels within an image or relevant portion of an image. Mean sharpness tends to be higher when an image is in focus. Variation in sharpness values over the course of a single scan may indicate a focus-related problem with the tool. In the example depicted in FIG. 5A, a problem arose near the top of the wafer in which the tool slowly went out of focus. In such a situation, corrective measures may be taken with respect to the inspection tool producing the images. Examples of corrective measures that could be taken in such a case include re-focusing the tool, re-calibrating the tool, repeating or correcting the image optimization process, or replacing faulty hardware causing the inspection instability. Some of these corrective measures may be implemented automatically, e.g., in response to the coded instructions 118. For example, an automatic re-focusing may be implemented by the coded instructions 118 when a drift in sharpness has been detected.

Many variations are possible on the concept illustrated in FIG. 5A. For example, mean sharpness values for different patch images may be determined with respect to vertical and horizontal direction in an image. Both the vertical and horizontal mean sharpness values may be plotted, e.g., on the same graph or side-by-side as a function of patch number. A pattern of difference between the mean vertical sharpness and mean horizontal sharpness may indicate an astigmatism problem in the inspection tool used to generate the patch images. Such a problem may be corrected by appropriate correction of the optics in the tool. In the case of an electron microscope, voltages at certain electrodes, referred to as "stig" voltages, may be adjusted to optimize the mean sharpness values and reduce a difference between the mean horizontal sharpness values and the mean vertical sharpness values.

Figure 5B:
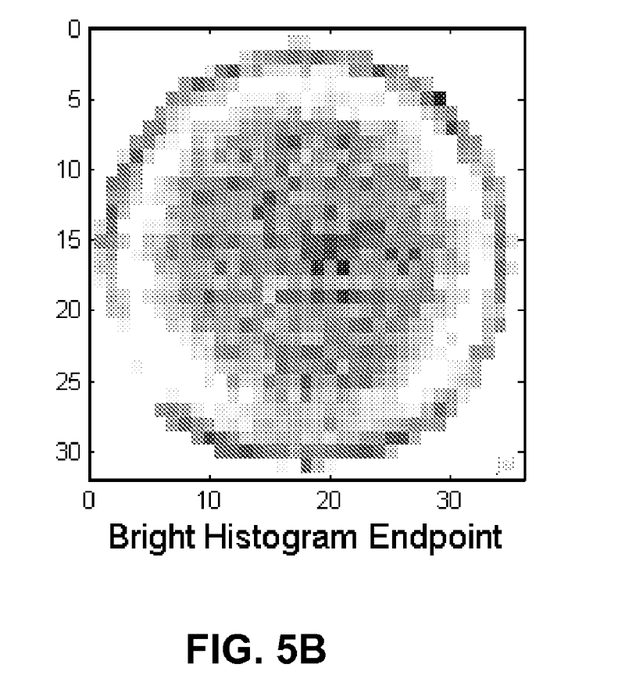
FIG. 5B is map depicting mean grey levels for patch images of dies on a wafer illustrating an example of monitoring stability of a substrate process according to an embodiment of the present invention.

As an example of diagnosing wafer processing, FIG. 5B depicts a map of mean grey levels for patch images of each die on a wafer. In this example, the mean gray levels are upper (bright) histogram endpoints in the patch images for each die. In FIG. 5B a circular pattern of brighter dies is discernable around the perimeter of the wafer. Such a pattern may indicate a process variation on the wafer. Corrective measures may be applied to one or more processing tools that processed the wafer before the wafer was inspected and the images were generated.

Figure 6A:
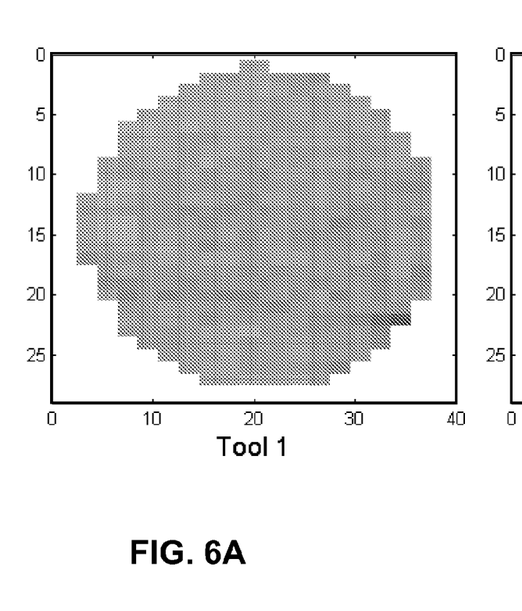
FIGS. 6A-6C are plots depicting mean sharpness for wafer inspections performed on three different tools illustrating the use of image quality information in the context of tool matching according to an embodiment of the present invention.
Figure 6B:
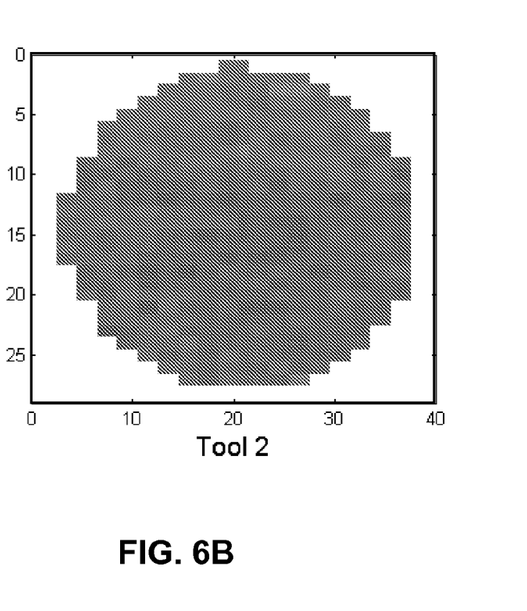
Figure 6C:
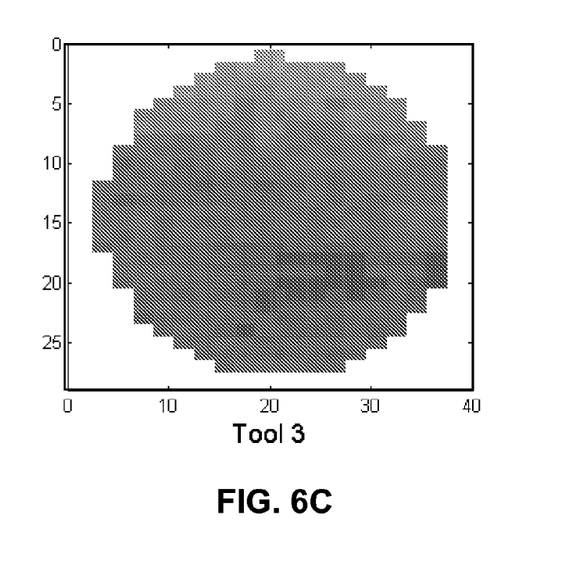

Embodiments of the present invention may also be used in the context of tool matching. As used herein, tool matching refers to adjustment of the parameters and/or settings of a tool or two or more different tools to reduce differences between images of the same substrate taken with different tools. For example, FIGS. 6A-6C depict sharpness maps for three different inspection tools. In the example depicted in FIGS. 6A-6C, the inspection tools were electron beam inspection tools. The performance of the tools may be compared with each other for the purpose of tool matching using such sharpness maps. For example, the sharpness map of FIG. 6A obtained with Tool 1 may be stored and used as a standard of comparison when Tools 2 and 3 are used to inspect the same substrate. The parameters of Tools 2 and 3 may be adjusted so that sharpness maps of the substrate obtained with Tools 2 and 3 match the sharpness map obtained with Tool 1.

A number of variations are possible on the above-described embodiments without departing from the scope of these teachings. For example, in alternative embodiments, extracting the image quality information may include determining a background noise level, image alignment magnitude and/or direction, die-to-die image correction magnitude, or frequency spectra obtained from image alignment during inspections. Based on analysis and graphing or mapping of the results of such analysis, e.g., as described above, performance of different tools may be compared with each other for the purpose of tool matching.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A method for monitoring the stability of an inspection or processing of a substrate, comprising:
    obtaining from an inspection tool one or more images of one or more portions of the substrate;
    extracting image quality information from the one or more images, wherein the image quality information is of a type that is ordinarily discarded after the image quality information is used to adjust the inspection tool;
    adjusting the inspection tool using the image quality information;
    performing an analysis of the image quality information independent of using the image quality information to adjust the inspection tool; and
    using results of the analysis to monitor stability of the inspection tool and/or to determine variation of a process performed on the substrate.

2. The method of claim 1 wherein the image quality information includes one or more quantities from the group of brightness, contrast, sharpness, background noise level, image alignment magnitude and/or direction, die-to-die image correction magnitude, or frequency spectra obtained from image alignment during inspections.

3. The method of claim 1 wherein extracting image quality information from the one or more images includes extracting the image quality information from the one or more images during the course of an inspection with the inspection tool.

4. The method of claim 1 wherein the one or more images include one or more patch images or swath images.

5. The method of claim 1 wherein extracting image quality information from the one or more images includes generating a histogram of image quality values for an image collected during the course of an inspection with the inspection tool and determining an average image quality value from the histogram.

6. The method of claim 5 wherein extracting image quality information from the one or more images includes determining a brightness, contrast or sharpness of one or more patch images or swath images.

7. The method of claim 6 wherein determining a brightness includes generating a histogram of grey levels for an image and determining an average grey level from the histogram.

8. The method of claim 7 wherein the average grey level is an average grey level for a die on the substrate.

9. The method of claim 5 wherein generating a histogram includes saving a histogram generated during an initial gain adjustment of the inspection tool.

10. The method of claim 1 wherein extracting the image quality information includes determining a bright and/or dark end point for grey levels of one or more images.

11. The method of claim 10 wherein the one or more images include one or more reference patch images and/or one or more defect patch images.

12. The method of claim 10 wherein the one or more images include one or more swath images.

13. The method of claim 1 wherein analyzing the image quality information includes storing the image quality information and analyzing the image quality information for variation.

14. The method of claim 1 wherein analyzing the image quality information includes determining a variation of the image quality information.

15. The method of claim 14, further comprising determining from the variation of the image quality information whether the variation results from the inspection tool or a process performed on the substrate.

16. The method of claim 14 wherein the variation is a variation with respect to time.

17. The method of claim 14 wherein the variation is a variation with respect to location on the substrate.

18. The method of claim 1, further comprising taking corrective measures in response to analysis of the image quality information.

19. The method of claim 18 wherein the corrective measures include varying one or more parameters of the inspection tool.

20. The method of claim 18 wherein the corrective measures include changing one or more parameters of a substrate process.

21. The method of claim 1 wherein analyzing the image quality information includes calculating average values of one or more quantities of image quality information for one or more images.

22. The method of claim 21 wherein using results of the analysis includes displaying an image representing the average values.

23. The method of claim 22 wherein the image is in the form of a graph.

24. The method of claim 22 wherein the image is in the form of a map.

25. A substrate inspection system, comprising:
    a substrate inspection tool having an image capture unit;
    a processor operably coupled to the image capture unit; and
    processor readable instructions executable on the processor, the instructions including
        an instruction for obtaining from the image capture unit one or more images of one or more portions of the substrate;
        an instruction for extracting image quality information from the one or more images, wherein the image quality information is of a type that is ordinarily discarded after the image quality information is used to adjust the inspection tool;
        an instruction for adjusting the inspection tool using the image quality information;
        an instruction for performing an analysis of the image quality information independent of using the image quality information to adjust the inspection tool; and
        an instruction for using results of the analysis to monitor stability of the inspection tool and/or to determine variation of a process performed on the substrate.

26. The system of claim 25 wherein the image capture unit is an optical microscope or electron microscope.

27. The system of claim 25, further comprising a memory operably coupled to the processor, wherein the instructions including an instruction for storing the image quality information.

28. A processor readable medium having embodied therein processor executable instructions for implementing a method for monitoring the stability of an inspection or processing of a substrate, the instructions comprising:

an instruction for obtaining from the image capture unit one or more images of one or more portions of the substrate;

an instruction for extracting image quality information from the one or more images, wherein the image quality information is of a type that is ordinarily discarded after the image quality information is used to adjust the inspection tool;

an instruction for adjusting the inspection tool using the image quality information;

an instruction for performing an analysis of the image quality information independent of using the image quality information to adjust the inspection tool; and     an instruction for using results of the analysis to monitor stability of the inspection tool and/or to determine variation of a process performed on the substrate.

29. The method of claim 1 wherein the image quality information is of a type that is used to adjust an initial image gain of the inspection tool.

30. The method of claim 1 wherein using the results of the analysis includes using the results of the analysis to determine variation of a process performed on the substrate.

* * * * *